US008521562B2

(12) United States Patent
Hernandez (10) Patent No.: US 8,521,562 B2
(45) Date of Patent: Aug. 27, 2013

(54) ILLNESS SPECIFIC DIAGNOSTIC SYSTEM

(76) Inventor: David Antonio Hernandez, Dade City, FL (US)

( * ) Notice: Subject to any disclaimer, the term of this patent is extended or adjusted under 35 U.S.C. 154(b) by 640 days.

(21) Appl. No.: 12/610,702

(22) Filed: Nov. 2, 2009

(65) Prior Publication Data

US 2010/0241472 A1    Sep. 23, 2010

Related U.S. Application Data

(60) Provisional application No. 61/162,468, filed on Mar. 23, 2009.

(51) Int. Cl.
*G06Q 50/00* (2012.01)
*G06Q 10/00* (2012.01)

(52) U.S. Cl.
USPC .................................................. 705/3; 705/2

(58) Field of Classification Search
USPC ......................................................... 705/2–3
See application file for complete search history.

(56) References Cited

U.S. PATENT DOCUMENTS 5,018,067 A     5/1991  Mohlenbrock et al.
6,000,828 A  *  12/1999 Leet ................................... 705/2

OTHER PUBLICATIONS

Kirkland, Evaluation of the ability of a battery of three in vitro genotoxicity tests to discriminate rodent carcinogens and non-carcinogens I. Sensitivity, specificity and relative predictivity, Mutation Research 584 (2005) 1-256.*

Lijmer, Empirical Evidence of Design-Related Bias in Studies of Diagnostic Tests, JAMA, Sep. 15, 1999—vol. 282, No. 11.*
Altman, Diagnostic tests 1: sensitivity and specificity, BMY 1994;308:1552.*
Christakis, Variation in Inpatient Diagnostic Testing and Management of Bronchiolitis, Pediatrics vol. 115 No. 4 Apr. 2005.*
International Search Report and the Written Opinion of the International Searching Authority issued on Dec. 14, 2010 in corresponding International Patent Application No. PCT/US2010/028260, entitled Illness Specific Diagnostic System, with an international filing date of Mar. 23, 2010.
Hernandez, D. A. et al. ISD Technology: A Strategy for Reduction of Low-Dose Radiation Exposure in Human Beings. 10th International Congress of the International Radiation Protection Association , Hiroshima, Japan, 2000.
Preliminary Report on Patentability from the International Bureau issued on Oct. 6, 2011 in corresponding International Patent Application No. PCT/US2010/028260, entitled Illness Specific Diagnostic System, with an international filing date of Mar. 23, 2010.
Hernandez, et al., ISD Technology: A Strategy for Reduction of Low-Dose Radiation Exposure in Human Beings, IRPA-10, 2000, p. 7-5.

* cited by examiner

*Primary Examiner* — Tran Nguyen
(74) *Attorney, Agent, or Firm* — Andriy Lytvyn; Courtney M. Dunn; Smith & Hopen, P.A.

(57) ABSTRACT

A method for diagnosing diseases in human subjects and a computer system implementing the method. The novel method uses historical patient medical records to create tables, which are used by a medical center to determine what diagnostic test is associated with confirmation of a disease in question. The method provides nonparametric, retrospective, disease cohort, rank ordered, weighted concatenation tables, which are unique to a disease and specific to the medical center where they are created, with prospective application. The method is more efficient and effective than presently used methods.

24 Claims, 7 Drawing Sheets

| Illness Specific Diagnostic Table |||||||
|---|---|---|---|---|---|---|
| Syncope & Collapse - DRG 312 |||||||
| Diagnostic Test | Negative | Positive | Equivocal | None | Total | Diagnosimetric Value |
| CPK | 235 | 26 | 8 | | 269 | 72.629 |
| CKMB | 262 | 11 | 1 | | 274 | 70.025 |
| Troponin | 187 | 20 | 4 | | 211 | 58.212 |
| CBC | 58 | 52 | 9 | | 119 | 44.665 |
| CMP | 55 | 54 | 5 | | 114 | 43.966 |
| Glu-POC | 53 | 31 | 26 | | 110 | 36.956 |
| BMP | 63 | 24 | 7 | | 94 | 31.117 |
| PT | 83 | 9 | | | 92 | 26.654 |
| PTT | 82 | 7 | | | 89 | 25.363 |
| Magnesium | 80 | 6 | | | 86 | 24.334 |
| TROP | 41 | 23 | | | 64 | 23.203 |
| CBC/Diff | 42 | 14 | | | 56 | 18.725 |
| TSH | 60 | 5 | | | 65 | 18.662 |
| Echo | 22 | 21 | | | 43 | 17.203 |
| BNP | 24 | 18 | 1 | | 43 | 16.397 |
| CT Brain | 38 | 9 | | | 47 | 15.030 |
| Folate | 37 | 8 | | | 45 | 14.236 |
| Lipid | 43 | 4 | | | 47 | 13.688 |
| Chest | 46 | 2 | | | 48 | 13.415 |
| UA | 36 | 4 | 5 | | 45 | 13.161 |
| US Echocardiogram | 29 | 5 | | | 34 | 10.518 |
| CT Brain w/o | 37 | 1 | | | 38 | 10.503 |
| GW POC | 1 | 18 | | | 19 | 10.034 |
| B12 | 35 | 1 | | | 36 | 9.972 |
| US Cartoid Duplex | 26 | 5 | | | 31 | 9.720 |
| Carotid US | 23 | 6 | | | 29 | 9.457 |
| X-Ray Chest 1 view | 31 | 1 | | | 32 | 8.907 |
| T4 Free | 20 | 3 | | | 23 | 7.041 |
| GLU POC | 7 | 8 | | | 15 | 6.247 |
| D Dimer | 13 | 4 | | | 17 | 5.699 |
| Brain | 8 | 6 | | | 14 | 5.434 |
| Phosphorous | 12 | 3 | | | 15 | 4.889 |
| URINALYSIS | 13 | 1 | | | 14 | 4.076 |
| Culture-Blood | 15 | | | | 15 | 4.074 |
| T4 Total | 11 | 1 | | | 12 | 3.535 |
| HSH (HCT) | | 6 | | | 6 | 3.270 |
| HSH (HGB) | | 6 | | | 6 | 3.270 |
| VIT B12 | 12 | | | | 12 | 3.263 |
| ABG | 1 | 5 | | | 6 | 2.998 |
| Digoxin | 4 | 3 | | | 7 | 2.724 |
| XR CHEST | 10 | | | | 10 | 2.721 |
| Drug Screen | 1 | 4 | | | 5 | 2.453 |
| GW POCII | 1 | 4 | | | 5 | 2.453 |
| H&H | 3 | 3 | | | 6 | 2.453 |
| MR Brain w/ wo cont. | 7 | 1 | | | 8 | 2.451 |
| SED RATE | 3 | 1 | 3 | | 7 | 2.179 |
| AMYLASE | 8 | | | | 8 | 2.178 |
| CRP | 1 | 3 | | | 4 | 1.909 |
| MRA BRAIN | 3 | 2 | | | 5 | 1.908 |
| BLOOD CULTURE | 7 | | | | 7 | 1.907 |
| Culture-Urine | 5 | | 2 | | 7 | 1.907 |
| LIPID PF | 7 | | | | 7 | 1.907 |
| MR Angio Neck w/o | 2 | 2 | | | 4 | 1.636 |
| Alcohol | 4 | 1 | | | 5 | 1.636 |
| Hgb A,C | 3 | 1 | 1 | | 5 | 1.636 |
| Neck | 4 | 1 | | | 5 | 1.636 |

*FIG. 4A*

| Diagnostic Test | Negative | Positive | Equivocal | None | Total | Diagnosimetric Test Value |
|---|---|---|---|---|---|---|
| LIPASE | 6 | | | | 6 | 1.635 |
| T3 Total | 6 | | | | 6 | 1.635 |
| DRUG URINE | 1 | 2 | | | 3 | 1.364 |
| D. DIMER | 3 | 1 | | | 4 | 1.364 |
| MRA NECK | 3 | 1 | | | 4 | 1.364 |
| US CAROTID | 3 | 1 | | | 4 | 1.364 |
| CK | 5 | | | | 5 | 1.363 |
| CT Abdomen | 5 | | | | 5 | 1.363 |
| CT Chest | 5 | | | | 5 | 1.363 |
| Liver | 5 | | | | 5 | 1.363 |
| AIC | | 2 | | | 2 | 1.092 |
| C URINE | | 2 | | | 2 | 1.092 |
| DRUG SERUM | | 2 | | | 2 | 1.092 |
| UF | | 2 | | | 2 | 1.092 |
| URINE CULTURE | | 2 | | | 2 | 1.092 |
| Hg A,C | 2 | 1 | | | 3 | 1.091 |
| MRA Head woC | 2 | 1 | | | 3 | 1.091 |
| CBK | 4 | | | | 4 | 1.091 |
| CT Pelvis | 4 | | | | 4 | 1.091 |
| MR BRAIN | 4 | | | | 4 | 1.091 |
| OCCULT BLD | 4 | | | | 4 | 1.091 |
| T3 Free | 4 | | | | 4 | 1.091 |
| T3 Uptake | 4 | | | | 4 | 1.091 |
| XR Chest 2V | 4 | | | | 4 | 1.091 |
| URINE DRUG SCREEN | 1 | 1 | | | 2 | 0.819 |
| ANA | 3 | | | | 3 | 0.818 |
| CRMB | 3 | | | | 3 | 0.818 |
| CT Chest PE w C | 3 | | | | 3 | 0.818 |
| DILANTIN | 3 | | | | 3 | 0.818 |
| Hb A,C | 2 | | 1 | | 3 | 0.818 |
| HEMOGLOBIN A1C | 3 | | | | 3 | 0.818 |
| LDH | 3 | | | | 3 | 0.818 |
| LIVER FX | 3 | | | | 3 | 0.818 |
| MR Angio Neck | 3 | | | | 3 | 0.818 |
| MRA Head wo cont | 3 | | | | 3 | 0.818 |
| NM Myocardial SPECT MH | 3 | | | | 3 | 0.818 |
| PSA | 3 | | | | 3 | 0.818 |
| PT/INR | 3 | | | | 3 | 0.818 |
| T3U | 3 | | | | 3 | 0.818 |
| T4 | 3 | | | | 3 | 0.818 |
| US Ext Lower Venous Doppler Bil | 3 | | | | 3 | 0.818 |
| XR L-Spine 4V | 3 | | | | 3 | 0.818 |
| ALCASTERNE | | 1 | | | 1 | 0.546 |
| ARC | | 1 | | | 1 | 0.546 |
| B. DIMER | | 1 | | | 1 | 0.546 |
| Cerebral Angiogram | | 1 | | | 1 | 0.546 |
| CT C-spine | | 1 | | | 1 | 0.546 |
| CUTTER URINE | | 1 | | | 1 | 0.546 |
| Homocystine | | 1 | | | 1 | 0.546 |
| IFE SERUM | | 1 | | | 1 | 0.546 |
| Protein EP | | 1 | | | 1 | 0.546 |
| US CAROTID | | 1 | | | 1 | 0.546 |
| C BC | 2 | | | | 2 | 0.546 |
| C Diff | 2 | | | | 2 | 0.546 |
| Cortisol | 1 | | 1 | | 2 | 0.546 |
| CT Abd | 2 | | | | 2 | 0.546 |
| CT Abd w/wo C | 2 | | | | 2 | 0.546 |
| CT C-Spine woc | 2 | | | | 2 | 0.546 |
| ESR | 2 | | | | 2 | 0.546 |
| HCG Qual | 2 | | | | 2 | 0.546 |
| MG | 2 | | | | 2 | 0.546 |

*FIG. 4B*

| Diagnostic Test | Negative | Positive | Equivocal | None | Total | Diagnosimetric Test Value |
|---|---|---|---|---|---|---|
| MR Brain w/o cont | 2 | | | | 2 | 0.546 |
| O&P | 2 | | | | 2 | 0.546 |
| Occult Bld | 1 | | 1 | | 2 | 0.546 |
| RA QUAL | 2 | | | | 2 | 0.546 |
| Stool CX | 1 | | 1 | | 2 | 0.546 |
| Venous | 2 | | | | 2 | 0.546 |
| Venous lower ext | 2 | | | | 2 | 0.546 |
| WBC Stool | 2 | | | | 2 | 0.546 |
| XR ABD, F/Upr | 2 | | | | 2 | 0.546 |
| XR Ribs | 2 | | | | 2 | 0.546 |
| Abdomen US | 1 | | | | 1 | 0.273 |
| Acetaminophen | 1 | | | | 1 | 0.273 |
| Aldosterone | 1 | | | | 1 | 0.273 |
| Ammonia | 1 | | | | 1 | 0.273 |
| Arterial US | 1 | | | | 1 | 0.273 |
| Bone | 1 | | | | 1 | 0.273 |
| CATECHOLAMINES, FRACTIONATED | 1 | | | | 1 | 0.273 |
| CT AND W/O | 1 | | | | 1 | 0.273 |
| CT Chest woc | 1 | | | | 1 | 0.273 |
| CT HEAD W/O | 1 | | | | 1 | 0.273 |
| CT Head wo cont | 1 | | | | 1 | 0.273 |
| CT Head/Brain | 1 | | | | 1 | 0.273 |
| CT PELVIS W | 1 | | | | 1 | 0.273 |
| CT Pelvis wc | 1 | | | | 1 | 0.273 |
| CTA Chest w/wo cont | 1 | | | | 1 | 0.273 |
| Digotin | 1 | | | | 1 | 0.273 |
| Drs Triage | 1 | | | | 1 | 0.273 |
| Foot | 1 | | | | 1 | 0.273 |
| HCG U Qual | 1 | | | | 1 | 0.273 |
| HCG URINE | 1 | | | | 1 | 0.273 |
| Head | 1 | | | | 1 | 0.273 |
| Humerus | 1 | | | | 1 | 0.273 |
| Knee | 1 | | | | 1 | 0.273 |
| LIPAISE | 1 | | | | 1 | 0.273 |
| Lower Ext US | 1 | | | | 1 | 0.273 |
| MR Angio Head | 1 | | | | 1 | 0.273 |
| MR Brain w/o | 1 | | | | 1 | 0.273 |
| MR C-Spine wo | 1 | | | | 1 | 0.273 |
| MRI BRAIN | 1 | | | | 1 | 0.273 |
| NM Scan | 1 | | | | 1 | 0.273 |
| PE Chest | 1 | | | | 1 | 0.273 |
| PENIN | 1 | | | | 1 | 0.273 |
| Prealbumin | 1 | | | | 1 | 0.273 |
| PT | 1 | | | | 1 | 0.273 |
| Renin | 1 | | | | 1 | 0.273 |
| Ribs | 1 | | | | 1 | 0.273 |
| Salicylate | 1 | | | | 1 | 0.273 |
| Shoulder | 1 | | | | 1 | 0.273 |
| U Microalbumin | 1 | | | | 1 | 0.273 |
| URD | 1 | | | | 1 | 0.273 |
| URINE EOSINOPHIS | 1 | | | | 1 | 0.273 |
| Urine-Chloride | 1 | | | | 1 | 0.273 |
| Urine-Creatinine | 1 | | | | 1 | 0.273 |
| Urine-Potassium | 1 | | | | 1 | 0.273 |
| Urine-Sodium | 1 | | | | 1 | 0.273 |
| US ABD | 1 | | | | 1 | 0.273 |
| US Abdomen Complete | 1 | | | | 1 | 0.273 |
| US CAROTID | 1 | | | | 1 | 0.273 |
| US CAROTID DUPLEX | 1 | | | | 1 | 0.273 |
| US Cartoid | 1 | | | | 1 | 0.273 |
| US ECHO | 1 | | | | 1 | 0.273 |

FIG. 4C

| Diagnostic Test | Negative | Positive | Equivocal | None | Total | Diagnosimetric Test Value |
|---|---|---|---|---|---|---|
| US Ext Lower Venous Duplex Bil | 1 | | | | 1 | 0.273 |
| US EXT LOWR | 1 | | | | 1 | 0.273 |
| US Thyroid | 1 | | | | 1 | 0.273 |
| VOLTAGE- GALED CALCIUM | 1 | | | | 1 | 0.273 |
| XR C-Spine 4V | 1 | | | | 1 | 0.273 |
| XR Elbow | 1 | | | | 1 | 0.273 |
| XR Wrist | 1 | | | | 1 | 0.273 |
| Microalbumin | | | 1 | | 1 | 0.000 |
| None | | | | 37 | 37 | 0.000 |
| PETIC | | | 2 | | 2 | 0.000 |
| URIC ACID | | | 2 | | 2 | 0.000 |
| Grand Total | 2132 | 482 | 81 | 37 | 2732 | |

ILLNESS SPECIFIC DIAGNOSTIC SYSTEM

CROSS REFERENCE TO RELATED APPLICATIONS

This application claims priority to currently pending U.S. Provisional Patent Application 61/162,468, filed Mar. 23, 2009, which is incorporated herein by reference.

FIELD OF INVENTION

This invention relates to the field of disease diagnosis.

BACKGROUND

Efficient orderly resource management of diagnostic tests in human disease is a resistant problem. Many diagnostic tests applied on human patient populations carry an element of risk. The decision matrix by which diagnosticians reduce symptoms to specific diagnostic tests varies due to differences in medical centers' diagnostic capacities. Health Maintenance Organization (HMOs), Preferred Physician Providers Organizations (PPOs), and others' methods introduced to reduce healthcare resource consumption by fiscal means have primarily failed as measured by the gross national product. What is needed in the medical arts is an improved method of disease diagnosis that is more effective and efficient than methods currently employed by diagnostic centers.

SUMMARY OF INVENTION

The present invention, called the Illness Specific Diagnostic System, includes an innovative scientific method to diagnosis diseases in human beings. System tables, created by the novel method, assist diagnosticians at a specific medical center select the most accurate and precise diagnostic test for a specific disease. The system does not use decision trees, but instead uses DIAGNOSIMETRICS™, the application of quantitative analysis to the art of disease diagnosis, as the method for construction of non-parametric, retrospective, disease-cohort, rank-ordered, weighted concatenation tables unique to a disease and specific to the medical center where they are created. The system destroys the myth of a single medical standard of care, and focuses the diagnostician as the individual most capable of diagnosing disease(s) in human beings. A computer system implementing the novel method is also presented.

In an embodiment, the method of determining the suitability of a diagnostic test for confirmation of a disease in humans comprises obtaining disease treatment results for patients grouped by disease in a Diagnostic Related Group (DRG) and obtaining diagnostic tests corresponding to each patient, each diagnostic test having a test result selected from the group comprising a positive result, a negative result, and an equivocal result. The method further comprises retrieving a first result for a first diagnostic test performed for each of the patients and a second result for a second diagnostic test performed for each of the patients, and transforming the first and second results to create a system value by solving for $$[\text{sign}]\left[\text{abs}\left(\log\left(X + \frac{1}{N}\right)\right) - \log(Y + N)\right] * (1 - (N - T)) * (X + T),$$

where X is the number of positive results for the first diagnostic test, Y is the number of negative results for the first diagnostic test, T is the total number of positive results, negative results, and equivocal results for the first diagnostic test, and N is the total number of positive results, negative results, and equivocal results for the first diagnostic test and positive results, negative results, and equivocal results for the second diagnostic test. The system value represents the suitability of the diagnostic test for confirmation of the disease.

In another embodiment, the computer system adapted to determine the suitability of a diagnostic test for confirmation of a disease in humans comprises a processor, and a tangible memory storage including software instructions that cause the computer system to perform: obtaining disease treatment results for patients grouped by disease in a Diagnostic Related Group (DRG) and obtaining diagnostic tests corresponding to each patient, each diagnostic test having a test result selected from the group comprising a positive result, a negative result, and an equivocal result. The software instructions cause the computer system to further perform: retrieving a first result for a first diagnostic test performed for each of the patients and a second result for a second diagnostic test performed for each of the patients, and transforming the first and second results to create a system value by solving for $$[\text{sign}]\left[\text{abs}\left(\log\left(X + \frac{1}{N}\right)\right) - \log(Y + N)\right] * (1 - (N - T)) * (X + T),$$

where X is the number of positive results for the first diagnostic test, Y is the number of negative results for the first diagnostic test, T is the total number of positive results, negative results, and equivocal results for the first diagnostic test, and N is the total number of positive results, negative results, and equivocal results for the first diagnostic test and positive results, negative results, and equivocal results for the second diagnostic test. The system value represents the suitability of the diagnostic test for confirmation of the disease, whereby the computer system determines the suitability of a diagnostic test for confirmation of a disease in humans.

In an additional embodiment, the method of determining the suitability of a diagnostic test for confirmation of a disease in humans comprises obtaining disease treatment results for patients grouped by disease in a Diagnostic Related Group (DRG) and obtaining diagnostic tests corresponding to each patient, each diagnostic test having a test result selected from the group comprising a positive result, a negative result, and an equivocal result. The method further comprises retrieving a first result for a first diagnostic test performed for each of the patients and a second result for a second diagnostic test performed for each of the patients, and transforming the first and second results to create a system value by solving for $$[\text{sign}]\left[\text{abs}\left(\log\left(X + \frac{1}{N}\right)\right) - \log\left(Y + \frac{1}{N}\right)\right]\left(1 - \frac{Z}{N}\right),$$

where X is the number of positive results for the first diagnostic test, Y is the number of negative results for the first diagnostic test, T is the total number of positive results, negative results, and equivocal results for the first diagnostic test, N is the total number of positive results, negative results, and equivocal results for the first diagnostic test and positive results, negative results, and equivocal results for the second diagnostic test, and Z is the number of patients not receiving the diagnostic test. The system value represents the suitability of the diagnostic test for confirmation of the disease.

In a further embodiment, the computer system adapted to determine the suitability of a diagnostic test for confirmation of a disease in humans comprises a processor, and a tangible memory storage including software instructions that cause the computer system to perform: obtaining disease treatment results for patients grouped by disease in a Diagnostic Related Group (DRG) and obtaining diagnostic tests corresponding to each patient, each diagnostic test having a test result selected from the group comprising a positive result, a negative result, and an equivocal result. The software instructions cause the computer system to further perform: retrieving a first result for a first diagnostic test performed for each of the patients and a second result for a second diagnostic test performed for each of the patients, and transforming the first and second results to create a system value by solving for $$[\text{sign}]\left[\text{abs}\left(\log\left(X+\frac{1}{N}\right)\right)-\log\left(Y+\frac{1}{N}\right)\right]\left(1-\frac{Z}{N}\right),$$

where X is the number of positive results for the first diagnostic test, Y is the number of negative results for the first diagnostic test, T is the total number of positive results, negative results, and equivocal results for the first diagnostic test, N is the total number of positive results, negative results, and equivocal results for the first diagnostic test and positive results, negative results, and equivocal results for the second diagnostic test, and Z is the number of patients not receiving the diagnostic test. The system value represents the suitability of the diagnostic test for confirmation of the disease, whereby the computer system determines the suitability of a diagnostic test for confirmation of a disease in humans.

BRIEF DESCRIPTION OF THE DRAWINGS

For a fuller understanding of the invention, reference should be made to the following detailed description, taken in connection with the accompanying drawings, in which.

DETAILED DESCRIPTION OF THE PREFERRED EMBODIMENT

In the following detailed description of the preferred embodiments, reference is made to the accompanying drawings, which form a part hereof, and within which are shown by way of illustration specific embodiments by which the invention may be practiced. It is to be understood that other embodiments may be utilized and structural changes may be made without departing from the scope of the invention.

The present invention, called the Illness Specific Diagnostic System, provides a system for the diagnosis of diseases in humans that is more effective and efficient than methods currently employed by diagnostic centers. Currently, physicians write prescriptions for diagnostic tests in response to patient symptoms. Then, the patient presents the prescriptions to a medical facility to perform the diagnostic test.

Under the present system, physicians perform a clinical assessment based on the patient's symptoms, and the diagnosticians arrive at one or more provincial disease diagnosis. The system creates system tables, which are used by the medical facility to determine what diagnostic test is associated with confirmation of the disease. The medical facility performs the diagnostic test, and the presence of the disease is confirmed or denied. Examples of medical facilities include but are not limited to hospitals, outpatient diagnostic centers, and clinics.

The system applies quantitative analysis to the art of disease diagnosis, as the method for construction of nonparametric, retrospective, disease cohort, rank ordered, weighted concatenation tables, unique to a disease and specific to the medical center where they are created, with prospective application.

Figure 1:
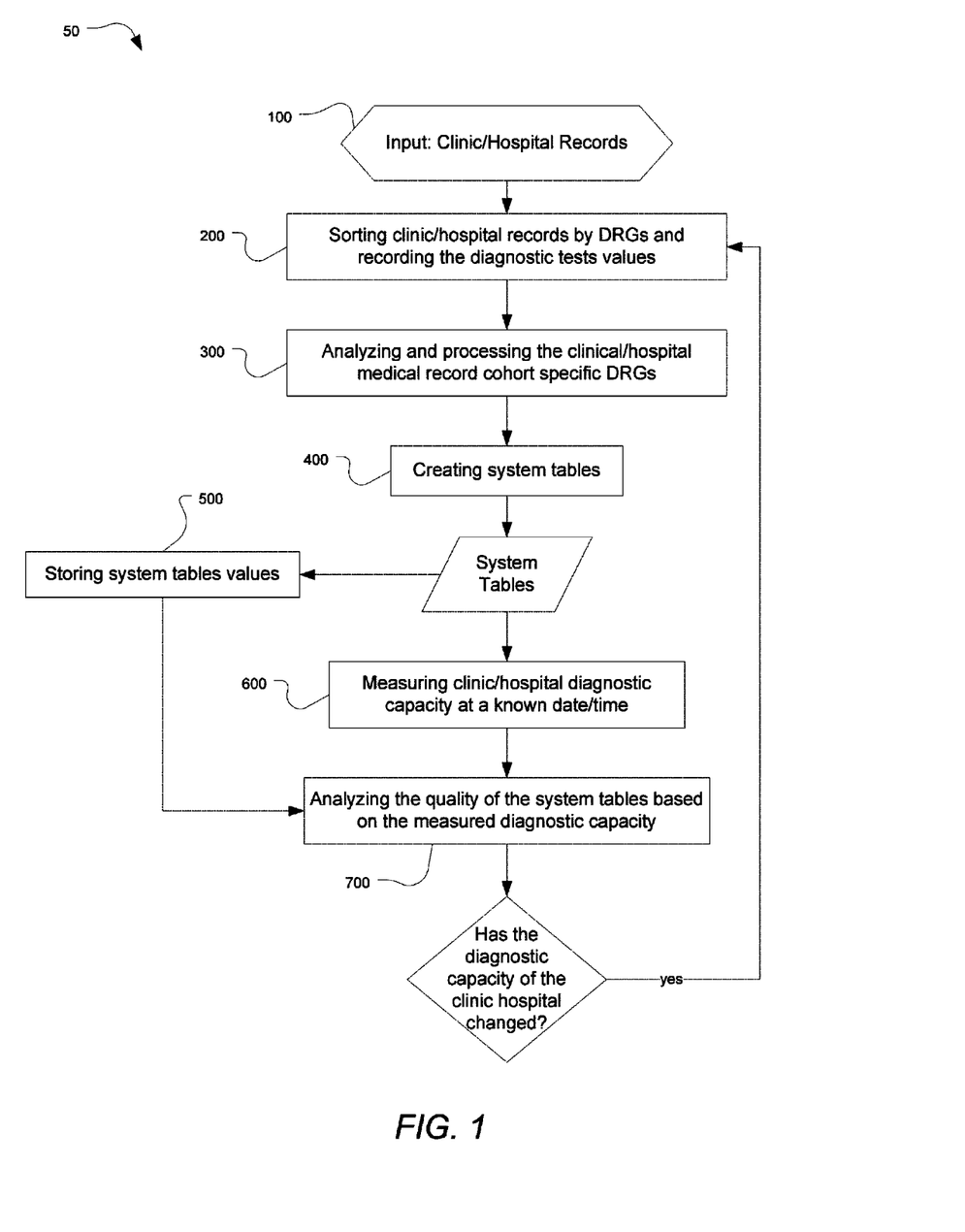
FIG. 1 is a flowchart showing an overview of the system.

FIG. 1 is a flowchart showing an overview of an embodiment of system 50. As shown in FIG. 1, a medical facility's records are gathered and received as input in operation 100. In the preprocessing of operation 200, the medical records are manually, or digitally, sorted by Diagnostic Related Groups (DRGs) and diagnostic test values are recorded. DRGs are used to classify medical records cases into cohorts, with each cohort expected to have similar hospital resource use. Diagnostic test values may be one of three possible values: positive, negative, or equivocal. In the main processing of operation 300, DIAGNOSIMETRICAL™ transformations, explained in detail below, are applied to the medical record cohort specific DRGs. Then, in the output processing of operation 400, system values, also referred to as DIAGNOSIMETRIC™ values, are created and may then be used to generate system tables. System values (and/or the corresponding system tables) are stored in digital or hard copy format in operation 500. Then, in the diagnostic capacity temporal stabilizer stage (operation 600), the medical facility's diagnostic capacity is measured at a known date and time. Then, in operation 700, system values (and/or the corresponding system tables) are checked for quality control based on the diagnostic capacity.

Figure 2:
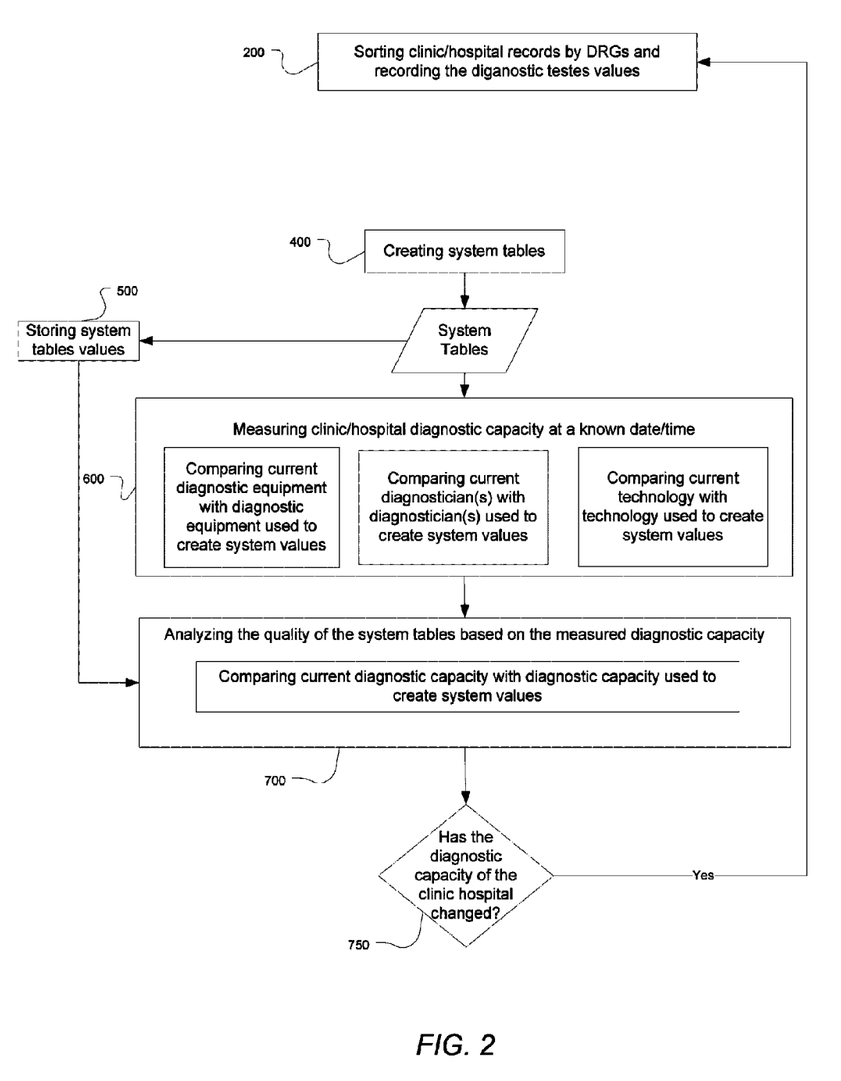
FIG. 2 is a flowchart showing an overview of the system's quality control feedback loop.

FIG. 2 is a flowchart showing an overview of the quality control feedback loop in an embodiment of system 50, which includes the diagnostic capacity temporal stabilizer (operation 600) and the quality control stage (operation 700). In operation 600, a number of factors are checked to determine if a change has occurred that requires changes to the system values (and the corresponding system tables). These factors may include changes in diagnostic equipment, changes in diagnosticians, and changes in technology. Operation 600 is time sensitive. In operation 700, it is determined if the diagnostic capacity of the medical facility has changed. If a change has occurred as determined in operation 750, then the system returns to operation 200 so that the new information can be processed and included in the creation of updated system values. This quality control feedback loop dynamically customizes the system table results to the target facility.

In an embodiment, referring back to FIG. 1, system 50 begins by establishing a target group of patients to be analyzed for disease treatment results. Next, in operation 100, data from the group of target patients' medical records is input into the system database. At the time of input, the system database software assigns a unique "Patient Key" to each patient record in order to maintain medical privacy. The following is an exemplary list of data taken from each patient's medical records:

A. Hospital Demographics
   1. Name
   2. Type
   3. Region
   4. Number of beds
B. Patient Demographics
   1. Case Number
   2. Date of Birth
   3. Religion
   4. Insurance Type
   5. Sex
   6. Occupation (pre-retirement)
   7. Tobacco use
   8. Admission Date
   9. Discharge Date
   10. Ethnicity
C. Diagnostic Procedure Characteristics
   1. DRG Number
   2. DRG Name
   3. DRG Modality
   4. Diagnostic Test Name (where the Diagnostic Test is the first use of a test)
   5. Diagnostic Test CPT
   6. Diagnostic Test Result—Positive, Negative, or Equivocal
   7. Physician Ordering the test
   8. Physician Generating the test result
   9. Evaluative Test Date (where the Evaluative Test is the second application of the same Diagnostic Test)
   10. Evaluative Test Result—Positive, Negative, or Equivocal Once the medical records have been received by system 50, the medical records are then sorted by DRGs in operation 200. The system database is scanned with the system analyzer in operation 300. The system analyzer works by creating and processing internal variables to track mathematical weighting ratios for the probabilities of a particular diagnostic test producing a desired diagnostic result.

To do this, the system analyzer generates a system value for each diagnostic test in the database. The system value ($D_x$) is conceptually based on an odds ratio given by ad/bc, where a is the number of patients with a positive test that have the disease in question (true positive), b is the number of patients with a positive test that do not have the disease in question (false positive), c is the number of patients with a negative test that have the disease in question (false negative), and d is the number of patients with a negative test that do not have the disease in question (true negative).

Specifically, the variables from the odds ratio are derived from a 2×2 contingency table as follows:

|  | True Positive (Patients with Disease) | True Negative (Patients without Disease) |
|---|---|---|
| Positive | a | b |
| Negative | c | d |

The conceptual basis is modified, and the positive odds ratio given by a/c. The odds are 100% for confirmation of the disease in question.

It is also possible to develop system values through the complementary opposite of a/c, which is the negative odds ratio given by b/d. This negative odds ratio is 100% for confirmation of no disease being present. As such, a/c represents the true positive values and b/d represents the true negative values. The example below generates positive system values, or DIAGNOSIMETRIC™ values, $D_p$ based on a/c. It is also possible to derive the same system value based on the use of b/d, which gives the negative system values $D_n$. Therefore, $D_p = D_n$ in so far as the system table generated is for disease confirmation $D_p$, and $D_n$ is for disease absence. Therefore, $D_p$ is the same system as $D_n$. There is a spectrum of permutation between $D_p$ and $D_n$ all of which are the same system, $D_p, D_n, \ldots D_x \ldots D_{nth}$. The use of $D_p$ is illustrated below.

The system value $D_p$ may be found by solving for $$D_p = \frac{a}{c} = [\text{sign}]\left[\text{abs}\left(\log\left(X + \frac{1}{N}\right)\right) - \log(Y + N)\right] * (1 - (N - T)) * (X + T),$$

where X is the number of positive test results for a specific diagnostic test, Y is the number of negative test results for the specific diagnostic test, T is the total number of test results for the specific diagnostic test (positive, negative, and equivocal), and N is the sum total number of test results for all diagnostic tests performed for this DRG. The system value may also be divided by factors of 10 to produce numbers that are easier to read and analyze. For example, for a divisor of 10,000, the system value would be given as $$\frac{[\text{sign}]\left[\text{abs}\left(\log\left(X + \frac{1}{N}\right)\right) - \log(Y + N)\right] * (1 - (N - T)) * (X + T)}{10,000}.$$

Figure 3:
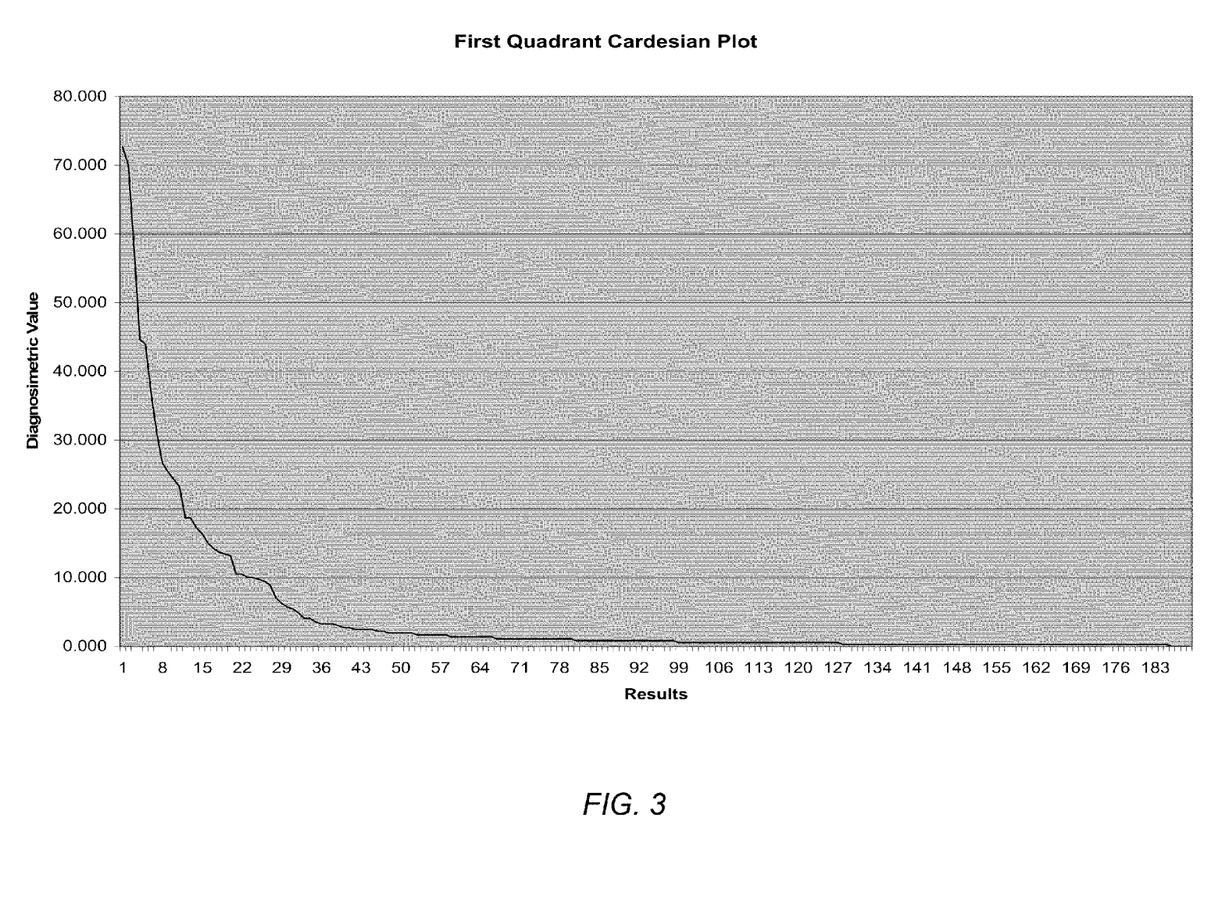
FIG. 3 is a graph illustrating the transformation of the positive system value (Dp), or system value, into the first quadrant Cartesian system. The ordinate axis is the system value, and the abscissa is the number of disease specific cohort tests results.
Figure 4A:
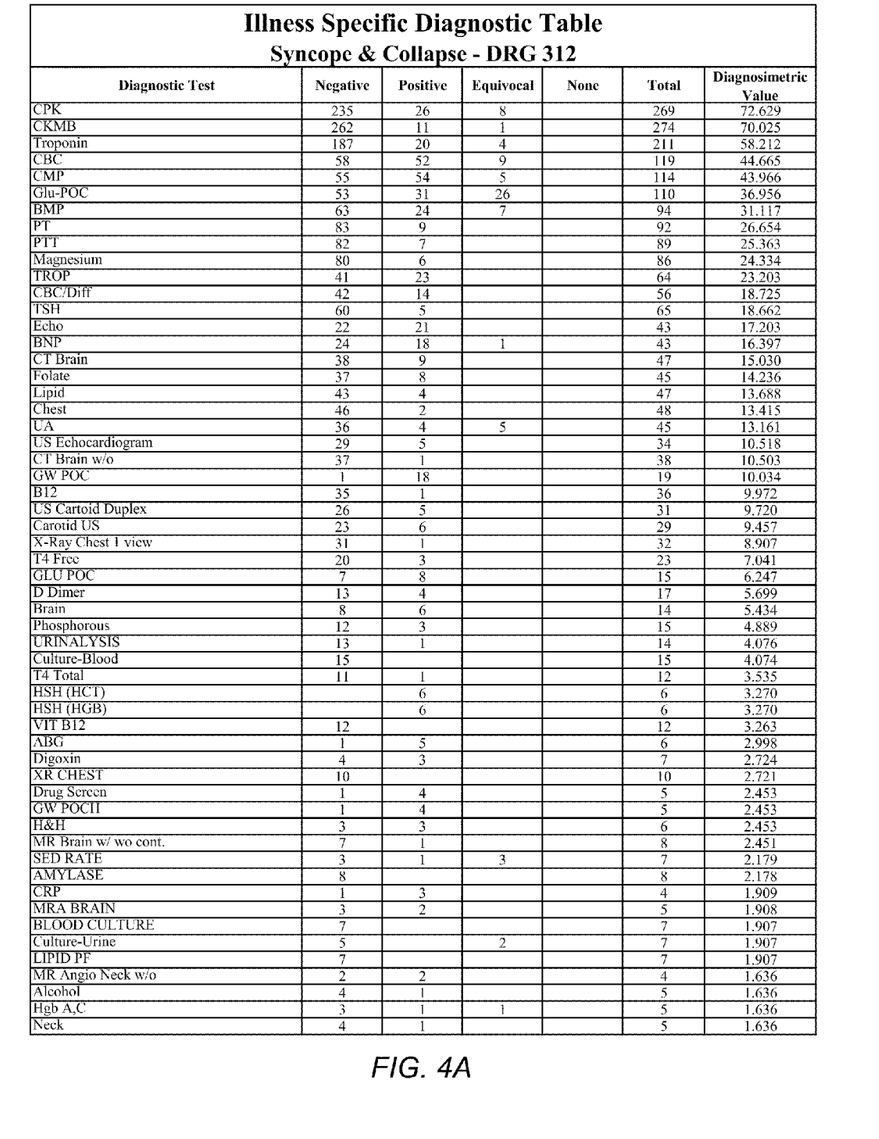
FIGS. 4A-4D are four continuous parts of an example system table in accordance with an embodiment of the present invention.
Figure 4B:
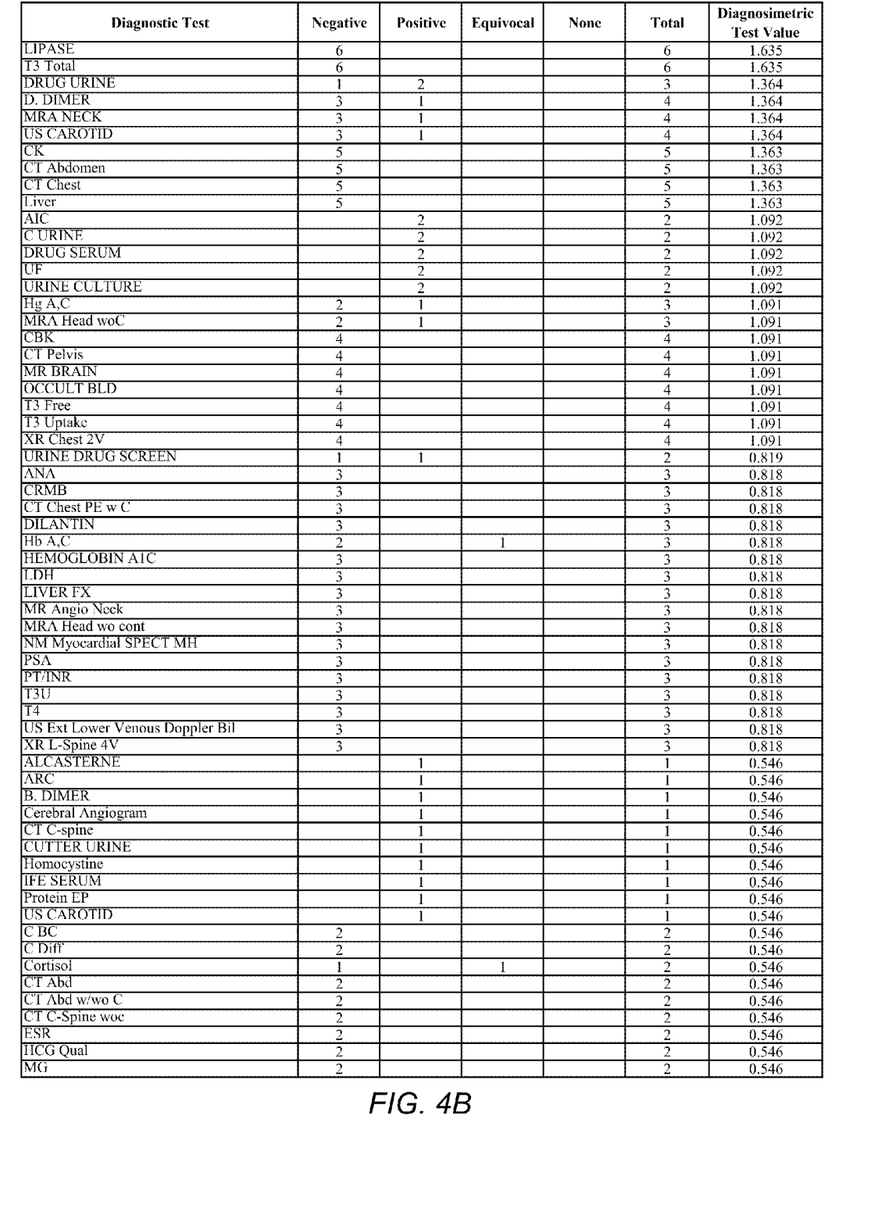
Figure 4C:
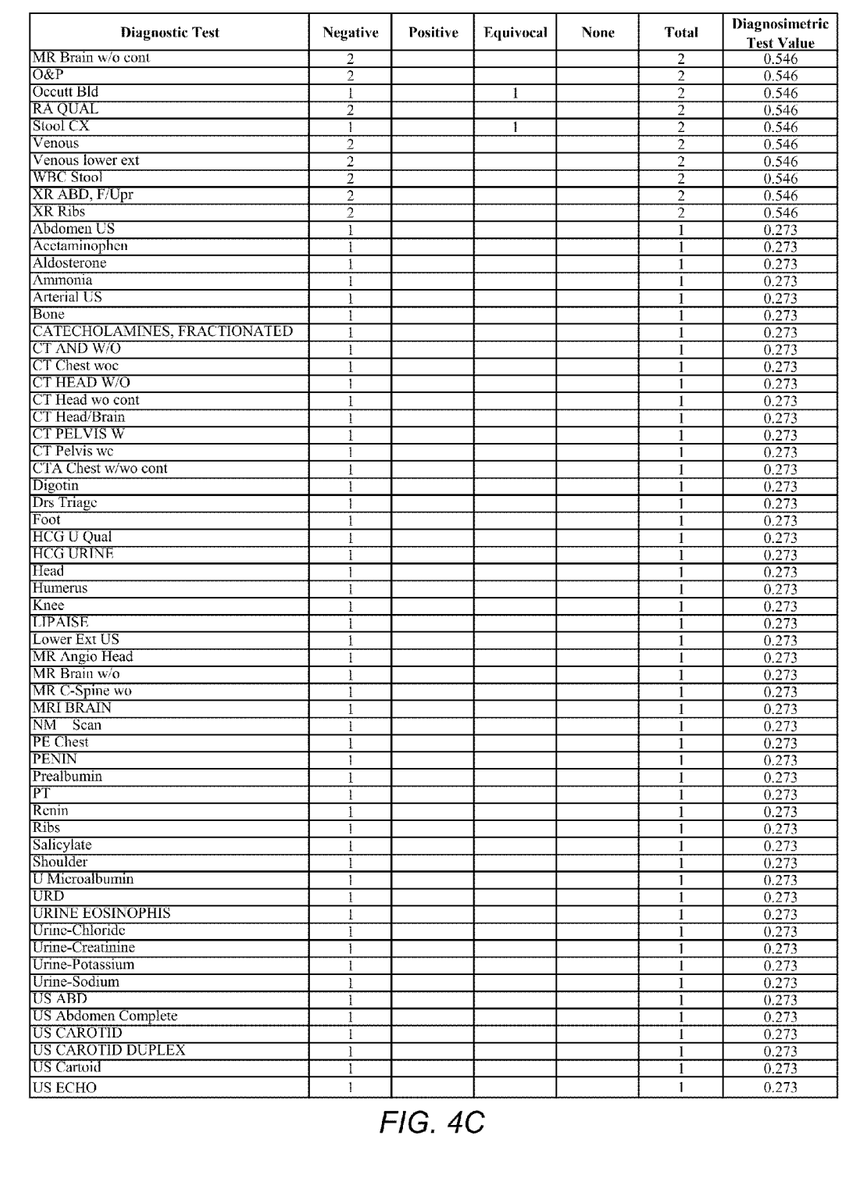
Figure 4D:
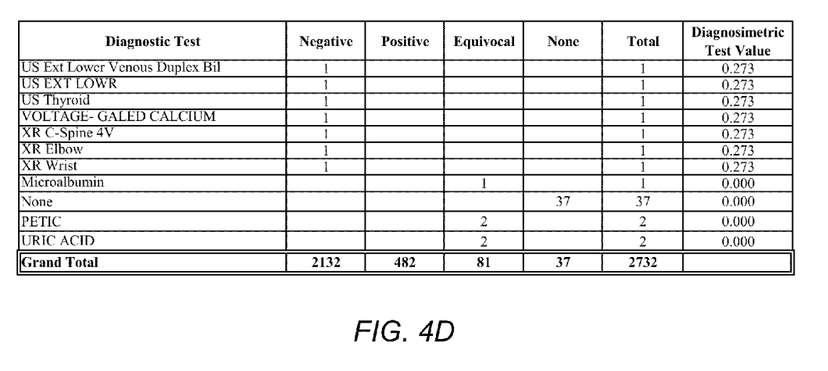

Each of the components of the above formulas are defined as follows:
1. $D_p$ is the composite weighted value given to each diagnostic test in the DRG cohort, and reflects the diagnostic test under investigation strength to identify a specific disease,
2. 
$$\left(\log\left(X + \frac{1}{N}\right)\right)$$

is a weighted (1/N=weight value) number sum of positive test values (X) the log of which inverses and moves the number (X+1/N) to travel in the same Cartesian quadrant and in the same direction as Y,
3. log(Y+N) is a weighted (N=weight value) number sum of negative test values (Y) the log of which inverses and moves the number (Y+N) to travel in the same Cartesian quadrant and in the same direction as X,
4. abs insures the result difference number of $$\left(\log\left(X + \frac{1}{N}\right)\right) - \log(Y + N)$$

is a positive integer,
5. (1−(N−T)) is the weight value of occurrence of the diagnostic test under analysis,
6. (X+T) is the weight value of positive strength of the diagnostic test under analysis, and
7. [sign] moves and inverts the periodic occurrence of the function $$\left[abs\left(\log\left(X+\frac{1}{N}\right)\right)-\log(Y+N)\right]*(1-(N-T))*(X+T)$$

to the first quadrant of the Cartesian coordinate system, as illustrated in the graph shown in FIG. 3.

Alternatively, the system value may be found by solving for $$\left(\frac{Z}{N}-1\right)*(1-(N-T))*(X+T),$$

where Z is the number of patients not receiving the diagnostic test. The expression $$\left(\frac{Z}{N}-1\right)$$

is equivalent to $$[sign]\left[abs\left(\log\left(X+\frac{1}{N}\right)\right)-\log\left(Y+\frac{1}{N}\right)\right]$$

and is an example of the algebraic manipulation of numbers. Ultimately, both expressions reveal the weighted strength of the diagnostic test in question to identify the presences, or absence of the disease under investigation.

Once the system values are calculated, system 50 then generates the system table (operation 400). The system table contains the recommended diagnostic tests to be run at the target facility per DRG-diagnosed disease. The system table is stored as a digital value or paper copy in operation 500. This results in the system table, which lists a number of diagnostic test procedures and the corresponding system value for a DRG disease treated by the target facility. Each DRG disease will have its own system table.

An example system table is shown in FIGS. 4A-4D. In this example, the results for syncope and collapse (DRG 312) at a medical facility are shown. At this particular medical facility, DRG 312 generated 144 medical records for a one year period. DRG 312 produced 2,732 diagnostic test results, which averages out to almost 20 diagnostic tests per medical record (case). The 2,732 diagnostic tests results split into 2,132 negative results, 482 positive results, 81 equivocal results, and 37 no-test-performed results, for a gross specificity of 0.18. The 2,732 test results came from 187 different types of diagnostic tests. In the example system table, the first column lists all of the diagnostic tests used at this facility on patients that were eventually diagnosed with syncope and collapse. The second, third, and fourth columns lists all the number of the negative test results, positive test results, and equivocal test results for each of the diagnostic tests, respectively. The fifth column lists the number of patients that were diagnosed with syncope and collapse that did not have any diagnostic test performed. The sixth column lists the total number of each patient having each diagnostic test and the last column lists the system value generated by system 50. The diagnostic test with the highest system value is listed first and the remaining diagnostic tests are listed by decreasing order of their system value. The higher the diagnostic test is on the list, the more likely the test is to appropriately identify the disease in question. In the example chart, a CPK (Creatine Phosphokinase) blood test is the diagnostic test most likely to appropriately identify syncope and collapse at this particular medical facility and the tests least likely to appropriately identify syncope and collapse at the facility are microalbumin, PETIC, and Uric Acid.

The subject medical facility can use this table to reduce drastically the number of diagnostic test performed at the facility. If a patient is thought to have syncope and collapse, the first two (or three) tests listed on the table may be performed. If these tests confirm the patient is free of the disease, then the diagnostician can move on to another potential diagnosis (and another system table for the new potential disease). The medical facility will not need to perform the other 185 (or 184) tests to confirm the presence of the disease, resulting in vast financial savings and a great improvement in the quality of medical care. Clinicians will be free from the burden of association of symptoms to diagnostic testing that proves time consuming and wasteful and physicians will have more time to focus on clinical evaluation and consultation to render a set of disease possibilities that the medical facility is expert to evaluate.

Based on existing medical physics evaluation record, a baseline value for each diagnostic instrument is obtained in operation 600. This baseline value is applied to future system evaluation, and is applied to existing values over time. The effect is to insure that changes in the medical facility's diagnostic capacity are reflected in the system value. Note that the diagnostic capacity is a measure of a medical facility's ability to diagnosis a disease. If the baseline value changes, a resort of the preprocessing occurs. Also note that diagnostic capacity is measured as follows:

| | |
|---|---|
| Identify the baseline: | 0 value = no change; 1 value = change |
| Diagnostic physicians: | 0 value = no change; 1 value = change |
| Technology: | 0 value = no change; 1 value = change |
| Diagnostic Equipment: | 0 value = no change; 1 value = change |

System table values and diagnostic capacity are then checked for stability and accuracy in operation 700. If both parameters are yes values, the system value is considered constant; if not, the table values are not constant, and a reevaluation is required.

It will be seen, that the advantages set forth above, and those made apparent from the foregoing description, are efficiently attained, and since certain changes may be made in the above construction without departing from the scope of the invention, it is intended that all matters contained in the foregoing description or shown in the accompanying drawings shall be interpreted as illustrative and not in a limiting sense.

It is also to be understood that the following claims are intended to cover all of the generic and specific features of the invention herein described, and all statements of the scope of the invention, which, as a matter of language, might be said to fall therebetween.

What is claimed is:

1. One or more non-transitory computer-readable media storing instructions which, when executed by one or more processors, cause the one or more processors to perform a method of selecting a diagnostic test for confirmation of a disease in a human subject comprising the steps of:

obtaining disease treatment results for a plurality of patients grouped by disease in a Diagnostic Related Group (DRG);

obtaining a plurality of diagnostic tests corresponding to each patient, each diagnostic test having a test result selected from the group comprising a positive result, a negative result, and an equivocal result;

retrieving a first set of result for a first diagnostic test performed for each of the plurality of patients;

retrieving a total number of all results obtained from the plurality of diagnostic tests;

transforming the first set of results to create a system value by solving for $$[\text{sign}]\left[\text{abs}\left(\log\left(X+\frac{1}{N}\right)\right)-\log(Y+N)\right]*(1-(N-T))*(X+T),$$

where X is the number of positive results for the first diagnostic test, Y is the number of negative results for the first diagnostic test, T is the total number of positive results, negative results, and equivocal results for the first diagnostic test, and N is the total number of all results obtained from the plurality of diagnostic test, wherein the system value represents a relative effectiveness of the first diagnostic test for confirmation of the disease;

performing the steps of retrieving a set of results for a diagnostic test and transforming the retrieved set of results into a system value representing a relative effectiveness of the diagnostic test for other diagnostic tests within the plurality; and sorting the diagnostic tests by relative effectiveness.

2. The one or more non-transitory computer-readable media of claim 1, further comprising:

generating a system table using the system value;

performing a clinical assessment based on a persons' symptoms;

determining a provincial disease diagnosis based on the clinical assessment;

determining the best diagnostic test for the determined provincial disease diagnosis using the system table; and confirming or denying the presence of the disease after performing the diagnostic test based on the results of the diagnostic test.

3. The one or more non-transitory computer-readable media of claim 2, wherein the plurality of patients are from a single medical facility.

4. The one or more non-transitory computer-readable media of claim 3, further comprising:

measuring the medical facility's diagnostic capacity at a first time;

measuring the medical facility's diagnostic capacity at a second time;

determining if a relevant change has occurred in the facility's diagnostic capacity between the measurement at the first time and the measurement at the second time;

analyzing the system value or the system table for quality control based on the diagnostic capacity of the medical facility; and re-calculating the system value, responsive to a change in the diagnostic capacity of the medical facility.

5. The one or more non-transitory computer-readable media of claim 4, wherein the relevant change is one or more of the changes chosen from the group consisting of a change in equipment, a change in diagnosticians, and a change in technology.

6. The one or more non-transitory computer-readable media of claim 1, further comprising:

determining a baseline value for a diagnostic instrument based on existing a medical physics evaluation record; and updating the system value responsive to a change in the baseline value.

7. A computer system adapted to determine the suitability of a diagnostic test for confirmation of a disease in humans comprising:

a processor; and a tangible memory storage including software instructions that cause the computer system to perform:

obtaining disease treatment results for a plurality of patients grouped by disease in a Diagnostic Related Group (DRG), obtaining a plurality of diagnostic tests corresponding to each patient, each diagnostic test having a test result selected from the group comprising a positive result, a negative result, and an equivocal result, retrieving a first result for a first diagnostic test performed for each of the plurality of patients, retrieving a second result for a second diagnostic test performed for each of the plurality of patients, and transforming the first and second results to create a system value by solving for $$[\text{sign}]\left[\text{abs}\left(\log\left(X+\frac{1}{N}\right)\right)-\log(Y+N)\right]*(1-(N-T))*(X+T),$$

where X is the number of positive results for the first diagnostic test, Y is the number of negative results for the first diagnostic test, T is the total number of positive results, negative results, and equivocal results for the first diagnostic test, and N is the total number of positive results, negative results, and equivocal results for the first diagnostic test and positive results, negative results, and equivocal results for the second diagnostic test, wherein the system value represents the suitability of the diagnostic test for confirmation of the disease, whereby the computer determines the suitability of a diagnostic test for confirmation of a disease in humans.

8. The computer system of claim 7, wherein the tangible memory storage further includes software instructions that cause the computer system to perform:

generating a system table using the system value.

9. The computer system of claim 8, wherein the plurality of patients are from a single medical facility.

10. The computer system of claim 9, wherein the tangible memory storage further includes software instructions that cause the computer system to perform:

measuring the medical facility's diagnostic capacity at a first time, measuring the medical facility's diagnostic capacity at a second time, determining if a relevant change has occurred in the facility's diagnostic capacity between the measurement at the first time and the measurement at the second time, analyzing the system value or the system table for quality control based on the diagnostic capacity of the medical facility, and re-calculating the system value, responsive to a change in the diagnostic capacity of the medical facility.

11. The computer system of claim 10, wherein the relevant change is one or more of the changes chosen from the group consisting of a change in equipment, a change in diagnosticians, and a change in technology.

12. The computer system of claim 7, wherein the tangible memory storage further includes software instructions that cause the computer system to perform:
   determining a baseline value for a diagnostic instrument based on existing a medical physics evaluation record, and
   updating the system value responsive to a change in the baseline value.

13. One or more non-transitory computer-readable media storing instructions which, when executed by one or more processors, cause the one or more processors to perform a method of diagnosing disease in a human subject comprising the steps of:
   obtaining disease treatment results for a plurality of patients grouped by disease in a Diagnostic Related Group (DRG);
   obtaining a plurality of diagnostic tests corresponding to each patient, each diagnostic test having a test result selected from the group comprising a positive result, a negative result, and an equivocal result;
   retrieving a first result for a first diagnostic test performed for each of the plurality of patients;
   retrieving s total number of all results obtained from the plurality of diagnostic test;
   transforming the first and second results to create a system value by solving for $$[\text{sign}]\left[\text{abs}\left(\log\left(X + \frac{1}{N}\right)\right) - \log\left(Y + \frac{1}{N}\right)\right]\left(1 - \frac{Z}{N}\right),$$

for where X is the number of positive results for the first diagnostic test, Y is the number of negative results for the first diagnostic test, N is the total number of all results obtained from the plurality of diagnostic tests, and Z is the number of patients not receiving the first diagnostic test, wherein the system value represents the relative effectiveness of the diagnostic test for confirmation of the disease;
   performing the steps of retrieving a set of results for a diagnostic test and transforming the retrieved set of results into a system value representing a relative effectiveness of the diagnostic test for other diagnostic tests within the plurality; and
   sorting the diagnostic tests by relative effectiveness.

14. The one or more non-transitory computer-readable media of claim 13, further comprising:
   generating a system table using the system value;
   performing a clinical assessment based on a persons' symptoms;
   determining a provincial disease diagnosis based on the clinical assessment;
   determining the best diagnostic test for the determined provincial disease diagnosis using the system table; and
   confirming of denying the presence of the disease after performing the diagnostic test based on the results of the diagnostic test.

15. The one or more non-transitory computer-readable media of claim 14, wherein the plurality of patients are from a single medical facility.

16. The one or more non-transitory computer-readable media claim 15, further comprising:
   measuring the medical facility's diagnostic capacity at a first time;
   measuring the medical facility's diagnostic capacity at a second time;
   determining if a relevant change has occurred in the facility's diagnostic capacity between the measurement at the first time and the measurement at the second time;
   analyzing the system value or the system table for quality control based on the diagnostic capacity of the medical facility; and
   re-calculating the system value, responsive to a change in the diagnostic capacity of the medical facility.

17. The one or more non-transitory computer-readable media of claim claim 16, wherein the relevant change is one or more of the changes chosen from the group consisting of a change in equipment, a change in diagnosticians, and a change in technology.

18. The one or more non-transitory computer-readable media of claim 13, further comprising:
   determining a baseline value for a diagnostic instrument based on existing a medical physics evaluation record; and
   updating the system value responsive to a change in the baseline value.

19. A computer system adapted to determine the suitability of a diagnostic test for confirmation of a disease in humans comprising:
   a processor; and
   a tangible memory storage including software instructions that cause the computer system to perform:
      obtaining disease treatment results for a plurality of patients grouped by disease in a Diagnostic Related Group (DRG),
      obtaining a plurality of diagnostic tests corresponding to each patient, each diagnostic test having a test result selected from the group comprising a positive result, a negative result, and an equivocal result,
      retrieving a first result for a first diagnostic test performed for each of the plurality of patients,
      retrieving a second result for a second diagnostic test performed for each of the plurality of patients, and
      transforming the first and second results to create a system value by solving for $$[\text{sign}]\left[\text{abs}\left(\log\left(X + \frac{1}{N}\right)\right) - \log\left(Y + \frac{1}{N}\right)\right]\left(1 - \frac{Z}{N}\right),$$

where X is the number of positive results for the first diagnostic test, Y is the number of negative results for the first diagnostic test, T is the total number of positive results, negative results, and equivocal results for the first diagnostic test, N is the total number of positive results, negative results, and equivocal results for the first diagnostic test and positive results, negative results, and equivocal results for the second diagnostic test, and Z is the number of patients not receiving the diagnostic test, wherein the system value represents the suitability of the diagnostic test for confirmation of the disease,
   whereby the computer determines the suitability of a diagnostic test for confirmation of a disease in humans.

20. The computer system of claim 19, wherein the tangible memory storage further includes software instructions that cause the computer system to perform:
   generating a system table using the system value.

21. The computer system of claim 20, wherein the plurality of patients are from a single medical facility.

22. The computer system of claim 21, wherein the tangible memory storage further includes software instructions that cause the computer system to perform:
- measuring the medical facility's diagnostic capacity at a first time,
- measuring the medical facility's diagnostic capacity at a second time,
- determining if a relevant change has occurred in the facility's diagnostic capacity between the measurement at the first time and the measurement at the second time,
- analyzing the system value or the system table for quality control based on the diagnostic capacity of the medical facility, and
- re-calculating the system value, responsive to a change in the diagnostic capacity of the medical facility.

23. The computer system of claim 22, wherein the relevant change is one or more of the changes chosen from the group consisting of a change in equipment, a change in diagnosticians, and a change in technology.

24. The computer system of claim 20, wherein the tangible memory storage further includes software instructions that cause the computer system to perform::
- determining a baseline value for a diagnostic instrument based on existing a medical physics evaluation record, and
- updating the system value responsive to a change in the baseline value.

\* \* \* \* \*